United States Patent [19]

Sugimori et al.

[11] Patent Number: 4,548,731
[45] Date of Patent: Oct. 22, 1985

[54] 2,4-DIFLUOROBENZENE DERIVATIVES

[75] Inventors: Shigeru Sugimori, Fujisawa; Tetsuhiko Kojima, Yokohama, both of Japan

[73] Assignee: Chisso Corporation, Ohsaka, Japan

[21] Appl. No.: 494,032

[22] Filed: May 12, 1983

[30] Foreign Application Priority Data

May 17, 1982 [JP] Japan .................................. 57-82654
Jul. 27, 1982 [JP] Japan .................................. 57-130867

[51] Int. Cl.⁴ .................... C09K 3/34; C07C 25/13; C07C 69/75
[52] U.S. Cl. ................. 252/299.63; 252/299.5; 560/1; 560/118; 570/129; 570/182
[58] Field of Search ............. 252/299.63, 299.5; 570/129, 182; 560/118, 1

[56] References Cited

U.S. PATENT DOCUMENTS

| | | | |
|---|---|---|---|
| 4,302,352 | 11/1981 | Eidenschink et al. | 252/299.5 |
| 4,340,498 | 7/1982 | Sugimori | 252/299.63 |
| 4,368,135 | 1/1983 | Osman | 252/299.63 |
| 4,399,298 | 8/1983 | Sugimori et al. | 252/299.63 |
| 4,400,293 | 8/1983 | Romer et al. | 252/299.63 |
| 4,405,488 | 9/1983 | Sugimori et al. | 252/299.63 |
| 4,415,470 | 11/1983 | Eidenschink et al. | 252/299.63 |
| 4,490,305 | 12/1984 | Eidenschink et al. | 252/299.5 |
| 4,502,974 | 3/1985 | Sugimori et al. | 252/299.63 |

FOREIGN PATENT DOCUMENTS

| | | | |
|---|---|---|---|
| 19665 | 12/1980 | European Pat. Off. | 252/299.63 |
| 74608 | 3/1983 | European Pat. Off. | 252/299.5 |
| 84194 | 7/1983 | European Pat. Off. | 252/299.63 |
| 3209178 | 9/1983 | Fed. Rep. of Germany | 252/299.63 |
| 53-75181 | 7/1978 | Japan | 252/299.65 |
| 56-149486 | 11/1981 | Japan | 252/299.63 |
| 57-154158 | 9/1982 | Japan | 252/299.63 |
| 57-165326 | 10/1982 | Japan | 252/299.63 |
| 58-13542 | 1/1983 | Japan | 252/299.63 |
| 58-23634 | 2/1983 | Japan | 252/299.63 |
| 58-118543 | 7/1983 | Japan | 252/299.63 |
| 58-126839 | 7/1983 | Japan | 252/299.63 |
| 2063287 | 6/1981 | United Kingdom | 252/299.63 |
| 2063250 | 6/1981 | United Kingdom | 252/299.63 |

OTHER PUBLICATIONS

Osman, M., et al, Mol. Cryst. Liq. Cryst., vol. 82, (Lett.), pp. 331–338, (1983).
Gray, G. W., et al, Mol. Cryst. Liq. Cryst., vol. 67, pp. 1–24, (1981).

*Primary Examiner*—Teddy S. Gron
*Attorney, Agent, or Firm*—Beall Law Offices

[57] ABSTRACT

Novel compounds having a small dielectric anisotropy value ($\Delta\epsilon$), a low viscosity and a small $\gamma$ value (ratio of saturation voltage to threshold voltage) indicating sharpness, and liquid crystal compositions containing the same are provided, which compounds are 2,4-difluorobenzene derivatives of trans-4-alkylcyclohexanes expressed by the general formula

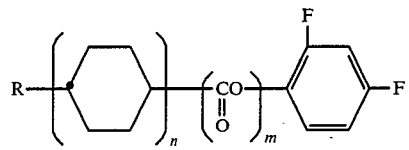

wherein n is 1 or 2, m is 0 or 1 and R represents an alkyl group of 1–10 carbon atoms.

9 Claims, No Drawings

2,4-DIFLUOROBENZENE DERIVATIVES

BACKGROUND OF THE INVENTION

1. Field of the Invention

This invention relates to new liquid crystal compounds having a low viscosity and being capable of improving sharpness as liquid crystal, and also liquid crystal compositions containing the same.

2. Description of the Prior Art

Liquid crystal display elements utilizing the optical anisotropy and dielectric anisotropy of liquid crystal substances are classified into various modes such as TN type (twisted nematic type), DS type (dynamic scattering type), guest-host type, DAP type, etc., depending on their display modes, and the properties of liquid crystal substances suitable to the respective uses vary. However, it is common to any of these liquid crystal substances that they are required to be stable to moisture, air, heat, light, etc. Further, it is desired that they exhibit a liquid crystal phase within a temperature range as broad as possible, around room temperature, and have a viscosity which is low enough not to reduce the response rate of display elements even at low temperature, and further have an optimal value of dielectric anisotropy ($\Delta\epsilon$) which varies depending on the kinds of display elements. However, substances which satisfy such conditions by their single use have not yet been found, and it is the present status that liquid crystal compositions obtained by blending some kinds of liquid crystal compounds or non-liquid crystal compounds have been used. In particular, the need for multiplex display to be used in liquid crystal display apparatus has recently been increasing, and it has been desired that as to such liquid crystals to be used for the multiplex display, the so-called $\gamma$ value (Vsat (saturation voltage)/Vth (threshold voltage)) indicating their sharpness be small.

SUMMARY OF THE INVENTION

The object of the present invention is to provide new compounds which are useful as a component constituting such liquid crystal compositions having a low viscosity and a superior sharpness.

The present invention resides in: 2,4-Difluorobenzene derivatives of trans-4-alkylcyclohexanes expressed by the general formula

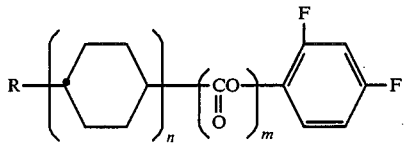

wherein n represents 1 or 2; m represents 0 or 1; and R represents an alkyl group of 1 to 10 carbon atoms, and liquid crystal compositions containing the same.

DETAILED DESCRIPTION OF THE INVENTION

The compounds of the present invention have a $\Delta\epsilon$ value as small as about +1 and a low viscosity, and when added to a liquid crystal composition, can lower the actuation voltages of the liquid crystal composition i.e. its threshold voltage and saturation voltage. Further, compounds of the formula (I) wherein m=1 and n=1, often enough are non-crystalline compounds or monotropic compounds, but since compounds of the formula (I) wherein m=1 and n=2 and those wherein m=0 and n=2 exhibit a nematic liquid phase over a broad temperature range up to high temperatures, blending them with one kind or more of other liquid crystals such as those of biphenyl system, phenylcyclohexane system, ester system, azoxy system, Schiff's base system or the like makes it possible to prepare a mixture of liquid crystals of a low viscosity capable of being actuated over from lower temperatures up to high temperatures. Further, when the compounds of the present invention are contained in a liquid crystal composition, its $\gamma$ value becomes small to make it possible to obtain liquid crystals more suitable to multiplex display.

Next, the preparation of the compounds of the present invention will be described below.

In the case of a compound (II) which is a compound of the formula (I) wherein m=1, firstly a trans-4-substituted cyclohexanecarboxylic acid corresponding to the objective compound is reacted with thionyl chloride to obtain a trans-4-substituted cyclohexanecarboxylic acid chloride, which is then reacted with 2,4-difluorophenol in the presence of pyridine to obtain the objective compound (II). These steps are shown by the following chemical equations:

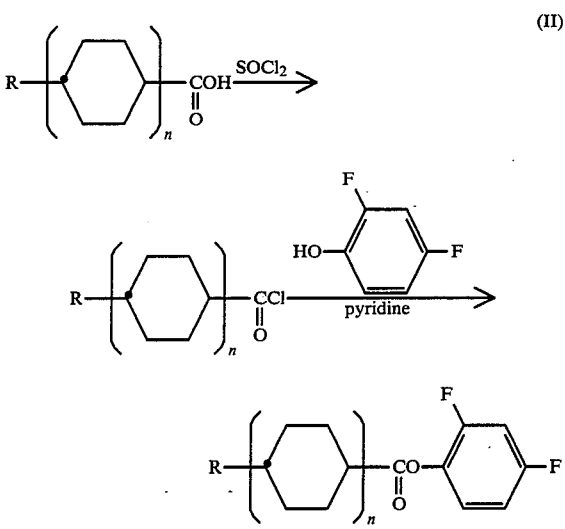

In this equation, R is defined as above.

Next, in the case of a compound (III) which is a compound of the formula (I) wherein m=0 and n=2, firstly, commercially available 2,4-difluorobromobenzene is reacted with metal magnesium to obtain 2,4-difluorobenzenemagnesium bromide, which is then reacted with a 4-(trans-4-alkylcyclohexyl)cyclohexanone to obtain a 2,4-difluoro-(4-trans-4-alkylcyclohexyl)cyclohexan-1-ol)benzene, which is then dehyldrated with potassium hydrogen sulfate to obtain a 2,4-difluoro-(4-(trans-4-alkylcyclohexyl)cyclohexene-1-yl)benzene, which is then catalytically reduced at ordinary temperature and ordinary pressure in the presence of Raney nickel in toluene solvent to obtain the objective 2,4-difluoro-(trans-4-(trans-4-alkylcyclohexyl)cyclohexyl)-benzene (III).

These steps are shown by the following chemical equations:

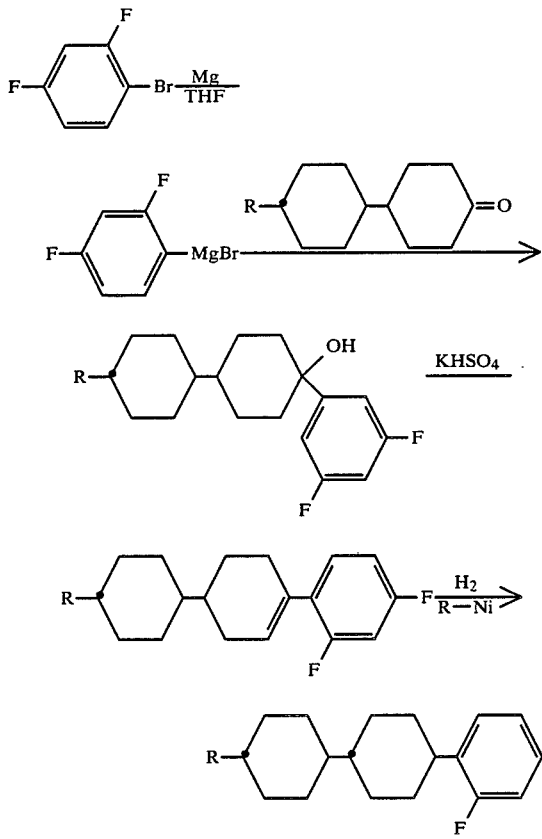

(III)

In these equations, R is defined as above.

The preparation of the compounds of the present invention and their use will be further described in details by way of Examples, but the present invention should not be construed to be limited thereby, but the present invention should be construed to include various modifications and applications thereof within the scope and spirit of claims.

EXAMPLE 1

Preparation of trans-4-(trans-4-ethylcyclohexyl)cyclohexanecarboxylic acid-2,4-difluorophenyl ester (a compound of the formula (I) wherein R=$C_2H_5$, m=1 and n=2)

Trans-4-(trans-4-ethylcyclohexyl)cyclohexanecarboxylic acid (2.4 g, 0.01 mol) and thionyl chloride (10 ml) were introduced into a flask and warmed to 50° C. to obtain a uniform reaction liquid in 3 hours, followed by distilling off excess thionyl chloride under reduced pressure to obtain as a remaining oily substance, trans-4-(trans-4-ethylcyclohexyl)cyclohexanecarboxylic acid chloride. This acid chloride was added to a solution obtained by dissolving 2,4-difluorophenol (1.3 g, 0.01 mol) in pyridine (10 ml), followed by adding dry toluene (100 ml), sufficiently shaking the mixture, allowing it to stand over night, pouring the reaction liquid into water, washing with 6N hydrochloric acid, then with 2N NaOH aqueous solution, washing with water till the aqueous layer became neutral, drying the toluene layer with anhydrous sodium sulfate, drying, distilling off toluene under reduced pressure and recrystallizing the remaining oily substance from ethanol to obtain the objective trans-4-(trans-4-ethylcyclohexyl)cyclohexanecarboxylic acid-2,4-difluorophenyl ester. Yield 2.1 g (60%). It had a C-N point (phase transition point) of 76.3°–76.7° C. and a N-I point of 151.7° C. C, N and I are defined as in Table 1.

EXAMPLES 2–11

Example 1 was repeated except that trans-4-(trans-4-ethylcyclohexyl)cyclohexanecarboxylic acid of Example 1 was replaced by trans-4-(trans-4-alkylcyclohexyl)cyclohexanecarboxylic acids having other alkyl groups or trans-4-alkylcyclohexanecarboxylic acids, to prepare compounds of the formula (II). The values of physical properties of these compounds are shown in Table 1 together with the results of Example 1.

TABLE 1

| | In formula (I) | | | Phase transition point in °C. | | |
|---|---|---|---|---|---|---|
| Example | R | n | m | C—N point C—Sm point m.p. | Sm—N point | N—I point |
| 1 | $C_2H_5$ | 2 | 1 | 76.3–76.7 | — | 151.7 |
| 2 | $C_3H_7$ | 2 | 1 | 86.1–86.8 | — | 179.8 |
| 3 | $C_4H_9$ | 2 | 1 | 74.5–75.5 | — | 172.5 |
| 4 | $C_5H_{11}$ | 2 | 1 | 77.6 | 88.2 | 177.9 |
| 5 | $C_2H_5$ | 1 | 1 | 27.8–28.8 | — | — |
| 6 | $C_3H_7$ | 1 | 1 | 69.2–70.4 | — | — |
| 7 | $C_4H_9$ | 1 | 1 | 28.2–29.1 | — | — |
| 8 | $C_5H_{11}$ | 1 | 1 | 44.0–44.7 | — | 8.8 |
| 9 | $C_6H_{13}$ | 1 | 1 | 33.1–33.7 | — | 11.3 |
| 10 | $C_7H_{15}$ | 1 | 1 | 38.8–39.8 | — | 18.6 |
| 11 | $C_8H_{17}$ | 1 | 1 | 41.5–42.5 | — | 18.5 |

Symbols C, N, S and I represent solid phase, nematic phase smetic phase and transparent phase respectively.

EXAMPLE 12

Preparation of 2,4-difluoro-(trans-4-(trans-4-pentylcyclohexyl)cyclohexyl)benzene (a compound of the formula (I) wherein R=$C_5H_{11}$, m=0 and n=2)

A solution obtained by dissolving commercially available 2,4-difluorobromobenzene (4.0 g, 0.020 mol) in tetrahydrofuran (10 ml) was reacted with magnesium (0.5 g, 0.020 mol) in nitrogen gas current to obtain 2,4-difluorobenzenemagnesium bromide. After the reaction liquid became uniform, a tetrahydrofuran solution (50 ml) of 4-(trans-4-pentylcyclohexyl)cyclohexanone (5.0 g, 0.020 mol) was rapidly added while the reaction temperature was kept at 30° C. or lower. The solution was refluxed at 60° C. for 2 hours, and 3N-hydrochloric acid (50 ml) was then added, followed by extracting the resulting product with toluene (200 ml) washing it with water, distilling off the solvent, adding potassium hydrogen sulfate (2 g), dehydrating with the sulfate at 200° C. in nitrogen atmosphere for 2 hours, cooling the reaction liquid, adding toluene (200 ml), filtering off potassium hydrogen sulfate, washing with water till the washing liquid became neutral, dehydrating the resulting material with anhydrous sodium sulfate, distilling off the solvent and recrystallizing from a solution of n-heptane and ethanol (1:1) to obtain crystals which were of 2,4-difluoro-(4-(trans-4-pentylcyclohexyl)cyclohexene-1-yl)benzene.

This product (0.4 g) was dissolved in toluene (10 ml), Raney nickel (0.2 g) was weighed in wet state and washed sufficiently with ethanol and then with toluene. This was added to the toluene solution obtained above, followed by catahytic reduction at ordinary temperature and ordinary pressure. When disappearance of the raw material was detected by gas chromatography, the reaction was stopped, followed by fittering off the catalyst, distilling off the solvent under reduced pressure and recrystallizing from n-heptane to obtain crystals of objective 2,4-difluoro-(trans-4-(trans-4-pentylcyclohexyl)cyclohexyl)benzene. Yield: 0.04 g. It had a C-Sm point of room temperaure or lower, a Sm-N point of 72.9° C. and a N-I point of 121.0° C.

EXAMPLES 13–15

Example 12 was repeated except that 4-(trans-4-pentylcyclohexyl)cyclohexanone in the operation of Example 12 was replaced by 4-(trans-4-alkylcyclohexyl)cyclohexanone having other alkyl groups, to prepare other 2,4-difluor-(trans-4-(trans-4-alkylcyclohexyl)cyclohexyl)benzenes. The values of physical properties of these products are shown in Table 2 together with those of Example 12.

TABLE 2

| | In formula (I) | | Phase transition point | | |
|---|---|---|---|---|---|
| Example | R | n | m | C—N point or C—Sm point | Sm—N point | N—I point |
| 13 | $C_3H_7$ | 2 | 0 | 70 | — | 126 |
| 14 | $C_4H_9$ | 2 | 0 | 46 | — | 125 |
| 12 | $C_5H_{11}$ | 2 | 0 | Room temp. or lower | 72.9 | 121.0 |
| 15 | $C_7H_{15}$ | 2 | 0 | 53 | 71 | 114 |

EXAMPLE 16 (USE EXAMPLE 1)

A liquid crystal composition (A) consisting of trans-4-propyl-(4'-cyanophenyl)cyclohexane 24% by weight, trans-4-pentyl-(4'-cyanophenyl)cyclohexane 36% by weight, trans-4-heptyl-(4'-cyanophenyl)cyclohexane 25% by weight and trans-4-pentyl-(4"-cyanobiphenyl)cyclohexane 15% by weight, had a nematic clearing point of 72.0° C., a viscosity at 20° C. of 28 cp, a Δε of +11.7 and an optical anisotropy value Δn of 0.140.

When this liquid crystal composition was sealed in a TN (twisted nematic) cell of 10 μm thick, the threshold voltage (Vth), the saturation voltage (Vsat) and the γ value were 1.84 V, 2.50 V and 1.36, respectively.

When 15 parts by weight of trans-4-pentylcyclohexanecarboxylic acid-2,4-difluorophenyl ester of Example 8 of the present invention was added to 85 parts by weight of the liquid crystal composition (A), the resulting liquid crystal composition had a nematic clearing point of 62.8° C., a viscosity at 20° C. of 26 cp. a Δε of +10.5 and an optical anisotropy value of 0.121. When this liquid crystal composition was measured in the same TN cell as above, the threshold voltage and the saturation voltage were 1.63 V and 2.19 V, respectively, that is, these voltages were both reduced. The γ value was 1.34, that is, improved by 0.02.

EXAMPLES 17 AND 18 (USE EXAMPLES 2 AND 3)

Use example 1 was repeated except that in place of trans-4-pentylcyclohexanecarboxylic acid-2,4-difluorophenyl ester, trans-4-hexylcyclohexanecarboxylic acid-2,4-difluorophenyl ester of Example 9 or trans-4-octylcyclohexanecarboxylic acid-2,4-difluorophenyl ester of Example 11 was added to the liquid crystal composition (A). The values of physical properties of the resulting liquid crystal compositions are shown in Table 3 together with the results of Use example 1.

TABLE 3

| | N—I point | η20 (cp) | Δε | Δn | Vth | Vsat | γ |
|---|---|---|---|---|---|---|---|
| Composition (A) alone | 72.0 | 28 | +11.7 | 0.140 | 1.84 | 2.50 | 1.36 |
| Use example 1 | 62.8 | 26 | +10.5 | 0.121 | 1.63 | 2.19 | 1.34 |
| 2 | 63.0 | 27 | +10.6 | 0.121 | 1.61 | 2.16 | 1.34 |
| 3 | 63.5 | 27 | +10.0 | 0.121 | 1.80 | 2.42 | 1.34 |

EXAMPLE 19 (USE EXAMPLE 4)

To 80 parts by weight of the liquid crystal composition (A) were added 5 parts by weight of 2,4-difluoro-(trans-4-(trans-4-propylcyclohexyl)cyclohexyl)benzene of Example 13, 10 parts by weight of 2,4-difluoro-(trans-4-(trans-4-butylcyclohexyl)cyclohexyl)benzene of Example 14 and 5 parts by weight of 2,4-difluoro-(trans-4-(trans-4-heptylcyclohexyl)cyclohexyl)benzene of Example 15.

The resulting liquid crystal composition had a nematic clearing point of 77.5° C., a viscosity at 20° C. of 32 cp, a Δε of +9.5 and an optical anisotropy value of 0.126. When this liquid crystal composition was measured in the same TN cell as above, the threshold voltage and the saturation voltage were 1.81 V and 2.44 V, respectively, that is, these voltages were both reduced; the N-I point was elevated; and the γ value was 1.35, that is, improved by 0.01.

What is claimed is:

1. 2,4-Difluorobenzene derivatives of trans-4-alkylcyclohexanes expressed by the general formula

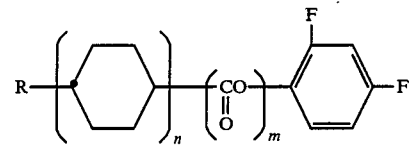

wherein m represents 0 or 1; and further wherein if m represents 1, then n represents 1 or 2 and if m represents 0, then n represents 2 and R represents an alkyl group of 1 to 10 carbon atoms.

2. Compounds according to claim 1, expressed by the general formula

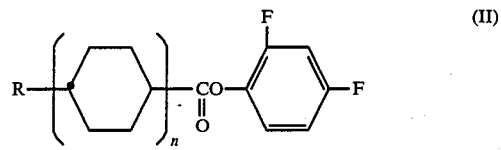

wherein n represents 1 or 2 and R represents an alkyl group of 1 to 10 carbon atoms.

3. Compounds according to claim 1, expressed by the general formula

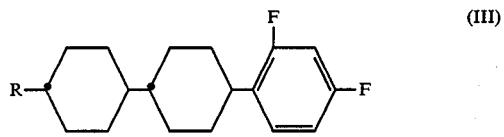

wherein R represents an alkyl group of 1 to 10 carbon atoms.

4. A liquid crystal material comprising a mixture of compounds at least one of which is compound according to claim 1.

5. Compounds according to claim 1, expressed by the general formula

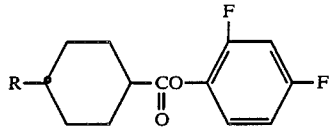

6. Compounds according to claim 1, expressed by the general formula

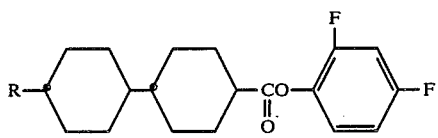

7. A liquid crystal composition comprising 85% by weight of a composition consisting of:
 24% by weight of trans-4-propyl-(4'-cyanophenyl)cyclohexane;
 36% by weight of trans-4-pentyl-(4'-cyanophenyl)cyclohexane;
 25% by weight of trans-4-heptyl-(4'-cyanophenyl)cyclohexane;
 15% by weight of trans-4-pentyl-(4"-cyanobiphenyl)cyclohexane; and
 15% by weight of trans-4-pentylcyclohexanecarboxylic acid-2,4-difluorophenyl ester.

8. A liquid crystal composition comprising 85% by weight of a composition consisting of:
 24% by weight of trans-4-propyl-(4'-cyanophenyl)cyclohexane;
 36% by weight of trans-4-pentyl-(4'-cyanophenyl)cyclohexane;
 25% by weight of trans-4-heptyl-(4'-cyanophenyl)cyclohexane; and
 15% by weight of trans-4-pentyl(4"-cyanobiphenyl)cyclohexane; and
 15% by weight of trans-4-hexylcyclohexanecarboxylic acid-2,4-difluorophenyl ester.

9. A liquid crystal composition comprising 80% by weight of a composition consisting of:
 24% by weight of trans-4-propyl-(4'-cyanophenyl)cyclohexane;
 36% by weight of trans-4-pentyl-(4'-cyanophenyl)cyclohexane;
 25% by weight of trans-4-heptyl-(4'-cyanophenyl)cyclohexane; and
 15% by weight of trans-4-pentyl-(4"-cyanobiphenyl)cyclohexane; and
 5% by weight of 2,4-difluoro-(trans-4-(trans-4-propylcyclohexyl)cyclohexyl)benzene;
 10% by weight of 2,4-difluoro-(trans-4-(trans-4-butylcyclohexyl)cyclohexyl)benzene; and
 5% by weight of 2,4-difluoro-(trans 4-(trans-4-heptylcyclohexyl)cyclohexyl)benzene.

* * * * *